United States Patent [19]

Creger

[11] Patent Number: 5,166,398

[45] Date of Patent: Nov. 24, 1992

[54] 4-OXY-SUBSTITUTED PHENOXYALKYL CARBOXYLIC ACID, ESTER, AND ALCOHOL DERIVATIVES AS ANTIHYPER-CHOLESTEROLEMIC AND ANTIATHEROSCLEROTIC AGENTS

[75] Inventor: Paul L. Creger, Ann Arbor, Mich.

[73] Assignee: Warner-Lambert Co., Mooris Plains, N.J.

[21] Appl. No.: 718,736

[22] Filed: Jun. 21, 1991

[51] Int. Cl.⁵ .................................... C07C 261/00
[52] U.S. Cl. .............................................. 560/32
[58] Field of Search ............... 560/32; 514/478, 543, 514/546, 547, 570

[56] References Cited

U.S. PATENT DOCUMENTS

| | | | |
|---|---|---|---|
| 4,413,011 | 11/1983 | Sircar et al. | 424/309 |
| 4,704,402 | 11/1987 | Abraham et al. | 514/543 |
| 4,882,357 | 11/1989 | Creger et al. | 514/622 |

FOREIGN PATENT DOCUMENTS 62-207236 9/1987 Japan .

Primary Examiner—Paul J. Killos
Attorney, Agent, or Firm—Francis J. Tinney

[57] ABSTRACT

Novel 4-oxy substituted phenoxyalkyl carboxylic acid, ester and alcohol derivatives are described, as well as methods for the preparation and pharmaceutical composition of same, which are useful in preventing the intestinal absorption of cholesterol and thus are useful in the treatment of hypercholesterolemia and atherosclerosis.

6 Claims, No Drawings

4-OXY-SUBSTITUTED PHENOXYALKYL CARBOXYLIC ACID, ESTER, AND ALCOHOL DERIVATIVES AS ANTIHYPER-CHOLESTEROLEMIC AND ANTIATHEROSCLEROTIC AGENTS

BACKGROUND OF THE INVENTION

The present invention relates to novel substituted 4-oxy-substituted phenoxyalkyl carboxylic acid, ester and alcohol derivatives useful as pharmaceutical agents, to methods for their production, to pharmaceutical compositions which include these compounds and a pharmaceutically acceptable carrier, and to a pharmaceutical method of treatment. More particularly, the novel compounds of the present invention lower low density lipoprotein cholesterol (LDL) and elevate high density lipoprotein cholesterol (HDL). Both of these effects afford protection from coronary heart disease.

The atheromatous plaque, which is the characteristic lesion of atherosclerosis, results from deposition of plasma lipids, mainly cholesteryl esters, in the intima of the arterial wall. Progressive enlargement of the plaque leads to arterial constriction and ultimately coronary heart disease. Two recent clinical trails have shown a causal relationship between serum levels of LDL- and HDL-cholesterol and coronary heart disease.

In 1984, the Lipid Research Clinics-Coronary Prevention Trial (LRC-CPPT) demonstrated for the first time that lowering LDL cholesterol would reduce coronary heart disease. Very recently the results of a five-year, 4,081 patient clinical trial published in the *New England Journal of Medicine*, 317, pp 1237–1245 (1987) demonstrated that the lipid regulating drug, gemfibrozil, reduced the rate of heart attack and sudden cardiac death by 34 percent in patients with elevated cholesterol levels. Gemfibrozil both lowers LDL and elevates HDL; but if the results from the LRC-CPPT study are utilized to estimate the expected reduction in incidence of heart attack and heart disease due to lowering of LDL, it amounts to approximately one-half of the effect actually observed. Thus, there appears to be little doubt as to the benefit of elevating HDL.

The compounds of this invention combine two mechanisms of action to achieve their improved activity in lowering LDL and elevating HDL. Not only do they show the same effects as gemfibrozil but, in addition, they inhibit the enzyme acyl-CoA:cholesterol acetyltransferase (ACAT).

Dietary cholesterol is absorbed from the intestinal lumen as free cholesterol which must be esterified with fatty acids. This reaction is catalyzed by ACAT. The resulting cholesteryl esters are packaged into the chylomicrons which are secreted into the lymph. Inhibitors of ACAT not only prevent absorption of dietary cholesterol but also prevent the reabsorption of cholesterol which has been released into the intestine through endogenous regulatory mechanisms, thus lowering LDL cholesterol levels and ultimately preventing the further development of atherosclerosis.

A series of phenoxyalkane acid derivatives of the formula:

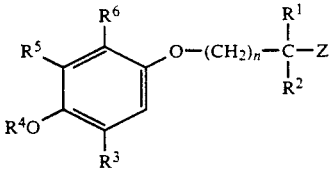

wherein $R^1$ and $R^2$ are the same or different lower alkyl groups;

$R^3$ is a hydrogen atom or a lower alkyl group;

$R^4$ is a hydrogen atom or a hydroxyl protective group;

$R^5$ is a hydrogen atom, an alkyl group, or a lower alkoxy group;

$R^6$ is a hydrogen atom, a lower alkyl group, or a lower alkoxy group;

Z is a group of the formula —COOR$^7$ (where $R^7$ is a hydrogen atom or a lower alkyl group) or a group of the formula —CH$_2$OR$^8$ (where $R^8$ is a hydrogen atom or an acyl group); and n is an integer of 1–10 is disclosed in JP 62-207236 as antioxidants which reduce lipid peroxide levels in rat liver microsomes and thus are postulated to be effective in the treatment of hyperlipemia in humans.

The present compounds have been chosen for their ability to lower LDL and elevate HDL and also to inhibit ACAT, and thus they possess two different mechanisms of action that complement each other. Thus, gemfibrozil speeds up the metabolism of LDL in the liver, and the excess cholesterol is released into the intestines via the bile. Normally a portion of this cholesterol is reabsorbed and ultimately recirculated in the form of new LDL. However, this is prevented in the presence of an ACAT inhibitor.

SUMMARY OF THE INVENTION

Accordingly, the present invention is a novel compound of Formula I

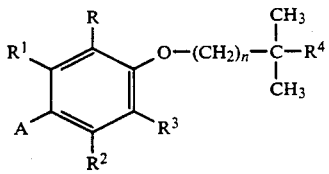

wherein A is —OR$^5$ wherein $R^5$ is alkyl of from one to four carbon atoms, or

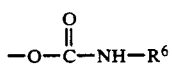

wherein $R^6$ is aryl;

R, $R^1$, $R^2$, and $R^3$ are each independently hydrogen or alkyl of from one to six carbon atoms provided at least two of R, $R^1$, $R^2$, or $R^3$ are alkyl of from one to six carbon atoms;

n is an integer of 3, 4, 5, or 6;

$R^4$ is —CO$_2$R$^8$ wherein $R^8$ is hydrogen, alkyl of from one to six carbon atoms, or benzyl, or —CH$_2$OH; or a pharmaceutically acceptable base addition salt thereof.

Additionally, the present invention is directed to a novel method of treating hypercholesterolemia or atherosclerosis comprising administering to a mammal in need of such treatment an acyl-coenzyme A:cholesterol acyltransferase-inhibitory effective amount of a compound of Formula Ia in unit dosage form.

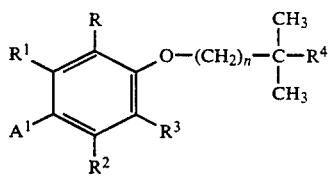

wherein $A^1$ is $-OR^5$ wherein $R^5$ is alkyl of from one to four carbon atoms,

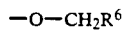

wherein $R^6$ is aryl,

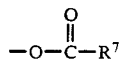

wherein $R^7$ is lower alkyl of from one to twenty carbon atoms, or

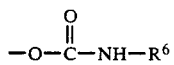

wherein $R^6$ is as defined above;

R, $R^1$, $R^2$, and $R^3$ are each independently hydrogen or alkyl of from one to six carbon atoms provided at least two of R, $R^1$, $R^2$, or $R^3$ are alkyl of from one to six carbon atoms;

n is an integer of 3, 4, 5, or 6;

$R^4$ is $-CO_2R^8$ wherein $R^8$ is hydrogen, alkyl of from one to six carbon atoms, or benzyl, or $-CH_2OH$; or a pharmaceutically acceptable base addition salt thereof.

Also, the present invention is directed to a pharmaceutical composition for treating hypercholesterolemia or atherosclerosis comprising an acyl-coenzyme A:-cholesterol acyl transferase-inhibitory effective amount of a compound of Formula I in combination with a pharmaceutically acceptable carrier.

Finally, the present invention is directed to methods for production of a compound of Formula I.

DETAILED DESCRIPTION OF THE INVENTION

In the compounds of Formula I or Ia, the term "alkyl" means a straight or branched hydrocarbon radical having from one to twenty carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, tridecyl, tetradecyl, pentadecyl, hexadecyl, heptadecyl, octadecyl, nonadecyl, eicosyl, and the like.

"Alkoxy" and "thioalkoxy" are O-alkyl or S-alkyl of from one to twenty carbon atoms as defined above for "alkyl".

The term "aryl" means an aromatic radical which is a phenyl group or a naphthyl group, unsubstituted or substituted by one to four substituents selected from alkyl as defined above, alkoxy as defined above, thioalkoxy as defined above, hydroxy or halogen.

"Halogen" is fluorine, chlorine, bromine or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

Certain of the compounds of Formula I or Ia are capable of further forming pharmaceutically acceptable base addition salts. All of these forms are within the scope of the present invention.

Pharmaceutically acceptable base addition salts are formed with metals or amines such as alkali and alkaline earth metals or organic amines. Examples of metals used as cations are sodium, potassium, magnesium, calcium and the like. Examples of suitable amines are N,N'-dibenzylethylenediamine, chloroprocaine, choline, diethanolamine, ethylenediamine, N-methylglucamine, and procaine (see, for example, Berge S. M., et al, *Journal of Pharmaceutical Science*, Vol. 66, pages 1–19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I is one wherein R, $R^1$, $R^2$, and $R^3$ are each independently hydrogen or methyl provided at least two of R, $R^1$, $R^2$, or $R^3$ are methyl.

Another preferred embodiment is a compound of Formula I wherein R, $R^1$, $R^2$, and $R^3$ are each independently hydrogen or methyl provided at least two of R, $R^1$, $R^2$, or $R^3$ are methyl and n is an integer of 3.

Particularly valuable are:

5-(4-Methoxy-2,5-dimethylphenoxy)-2,2-dimethylpentanoic acid, methyl ester;

5-(4-Methoxy-2,5-dimethylphenoxy)-2,2-dimethylpentanoic acid;

5-(4-Butoxy-2,5-dimethylphenoxy)-2,2-dimethylpentanoic acid, methyl ester;

5-(4-Butoxy-2,5-dimethylphenoxy)-2,2-dimethylpentanoic acid;

5-(4-Ethoxy-2,5 dimethylphenoxy)-2,2-dimethylpentanoic acid, methyl ester;

5-(4-Ethoxy-2,5-dimethylphenoxy)-2,2-dimethylpentanoic acid;

5-[4-(2,2-Dimethyl-1-oxopropoxy)-2,3,6-trimethylphenoxy]-2,2-dimethylpentanoic acid, methyl ester;

2,2-Dimethyl-5-[2,3,5-trimethyl-4-(phenylmethoxy)-phenoxy]pentanoic acid, methyl ester;

2,2-Dimethyl-5-[2,3,5-trimethyl-4-(phenylmethoxy)-phenoxy]pentanoic acid;

2,2-Dimethyl-5-[2,3,5 trimethyl-4-phenylmethoxy)-phenoxy]pentanol;

5-[3,5-Dimethyl 4-(phenylmethoxy)phenoxy]-2,2-dimethylpentanoic acid, methyl ester;

5-[3,5-Dimethyl-4-(phenylmethoxy)phenoxy]-2,2-dimethylpentanoic acid;

5-[2,5-Dimethyl 4 (phenylmethoxy)phenoxy]-2,2-dimethylpentanoic acid, methyl ester;

5-[2,5-Dimethyl-4-(phenylmethoxy)phenoxy]-2,2-dimethylpentanoic acid; and

5-[4-[[[[2,6-Bis(1-methylethyl)phenyl]-amino]carbonyl]oxy]-2,5 dimethylphenoxy]-2,2-dimethylpentanoic acid, methyl ester; or a pharmaceutically acceptable base addition salt thereof.

The compounds of the present invention were tested for their ability to inhibit the esterification of cholesterol by the enzyme acyl-CoA:cholesterol acyltransferase (ACAT). The data in the table below is expressed as $IC_{50}$ values, i.e., the concentration of test compound required to inhibit cholesteryl oleate formation to 50% of control. The data in the table shows the ability of representative compounds of the present invention to potently inhibit ACAT.

The in vitro test employed is more fully described in Field, F. J. and Salome, R. G., *Biochemica et Biophysica Acta*, Vol. 712, pages 557–570 (1982). The assay evaluates the ability of a test compound to inhibit the esterification of cholesterol using endogenous cholesterol of a rabbit intestinal microsomal fraction and exogenous $^{14}C$-oleoyl-CoA as reactants.

Additionally, the elevation of HDL is reported in the table as a ratio of the elevation of HDL effected by a dose of 50 mg/kg of the test drug divided by the elevation of HDL effected by a 50 mg/kg dose of gemfibrozil which is used as a control in each experiment.

$$HDL \text{ elevation} = \frac{\Delta HDL \text{ test drug}}{\Delta HDL \text{ gemfibrozil}}$$

Thus, a figure of 1 means that the test drug was as effective as gemfibrozil in elevating HDL. Values greater than 1 suggest that the test drug is more effective than gemfibrozil. The test procedure is described in U.S. Pat. No. 4,413,011 which is herein incorporated by reference.

TABLE 1

Biological Activity of Compounds of Formula I and Ia

| Example | Compound | $IC_{50}$ (μmoles) | Δ HDL Test Compound / Δ HDL Gemfibrozil |
|---|---|---|---|
| 2 | 5-(4-Butoxy-2,5-dimethylphenoxyl)-2,2-dimethylpentanoic acid, methyl ester | | 0.85 |
| 3 | 5-(4-Ethoxy-2,5-dimethylphenoxy)-2,2-dimethylpentanoic acid, methyl ester | | 1.2 |
| 4 | 5-(4-Methoxy-2,5-dimethylphenoxy)-2,2-dimethylpentanoic acid | | 1.2 |
| 5 | 5-(4-Butoxy-2,5-dimethylphenoxy)-2,2-dimethylpentanoic acid | | 0.9 |
| 6 | 5-(4-Ethoxy-2,5-dimethylphenoxy)-2,2-dimethylpentanoic acid | | 1.4 |
| 7 | 5-[4-(2,2-Dimethyl-1-oxopropoxy)-2,3,6-trimethylphenoxy]-2,2-dimethylpentanoic acid, methyl ester | | 1.1 |
| 8 | 2,2-Dimethyl-5-[2,3,5-trimethyl-4-(phenylmethoxy)phenoxy]pentanoic acid, methyl ester | | 1.0 |
| 9 | 2,2-Dimethyl-5-[2,3,5-trimethyl-4-(phenylmethoxy)phenoxy]pentanoic acid | | 0.9 |
| 10 | 2,2-Dimethyl-5-[2,3,5-trimethyl-4-(phenylmethoxy)phenoxy]pentanol | | 0.9 |
| 11 | 5-[3,5-Dimethyl-4-(phenylmethoxy)phenoxy]-2,2-dimethylpentanoic acid, methyl ester | | 1.2 |
| 14 | 5-[3,5-Dimethyl-4-(phenylmethoxy)phenoxy]-2,2-dimethylpentanoic acid | | 1.0 |
| 15 | 5-[4-[[[[2,6-Bis(1-methylethyl)phenyl]-amino]carbonyl]oxy]-2,5-dimethylphenoxy]-2,2-dimethylpentanoic acid, methyl ester | >5 | |

A compound of Formula Ia

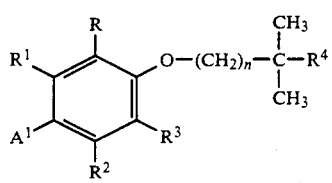

wherein $A^1$ is $-OR^5$ wherein $R^5$ is alkyl of from one to four carbon atoms,

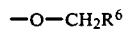

wherein $R^6$ is aryl

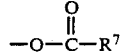

wherein $R^7$ is lower alkyl of from one to twenty carbon atoms, or,

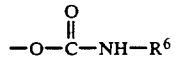

wherein $R^6$ is or defined above;

R, $R^1$, $R^2$, and $R^3$ each independently hydrogen or alkyl of from one to six carbon atoms provided at least two of R, $R^1$, $R^2$, or $R^3$ are alkyl of from one to six carbon atoms;

n is an integer of 3, 4, 5, or 6;

$R^4$ is $-CO_2R^8$ wherein $R^8$ is hydrogen, alkyl of from one to six carbon atoms, or benzyl, or $-CH_2OH$;

or a pharmaceutically acceptable base addition salt thereof may be prepared by reacting a compound of Formula II

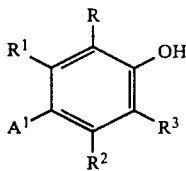   II wherein R, $R^1$, $R^2$, and $R^3$ and $A^1$ are as defined above with a compound of Formula III

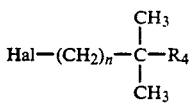   III wherein Hal is halogen and n and $R^4$ are as defined above, in the presence of a base such as, for example, an alkali metal, alkaline earth metal carbonate or hydroxide for example, potassium carbonate, sodium carbonate, a metal hydride such as, for example, sodium hydride and the like and a solvent such as, for example, acetontrile, dimethylsulfoxide and the like at about room temperature to about the reflux temperature of the solvent for about 1 hour to about 24 hours to afford a compound of Formula Ia. Preferably, the reaction is carried out in the presence of potassium carbonate and acetonitrile at about room temperature for about 24 hours.

Preferably, a compound of Formula Ib

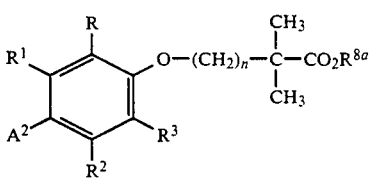   Ib wherein $A^2$ is $-OR^5$ wherein $R^5$ alkyl of from one to four carbon atoms, $-OCH_2R^6$ where $R^6$ is aryl, or

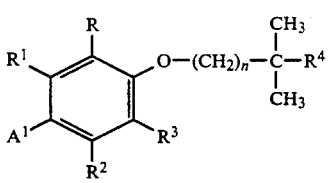   Ia wherein $R^7$ is alkyl of from one to twenty carbon atoms, $R^{8a}$ is alkyl of from one to six carbon atoms, or benzyl, and R, $R^1$, $R^2$, and $R^3$ are as defined above may be prepared by reacting a compound of Formula IIa

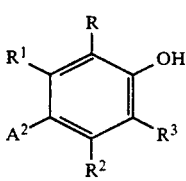   IIa wherein R, $R^1$, $R^2$, $R^3$, and $A^2$ are as defined above with a compound of Formula IIIa

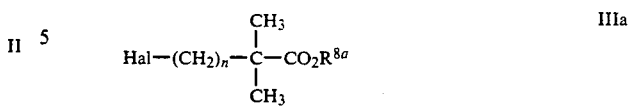   IIIa wherein Hal, n, and $R^{8a}$ are as defined above, using the methodology used to prepare a compound of Formula Ia from a compound of Formula II and Formula III to afford a compound of Formula Ib.

Preferably, a compound of Formula Ic

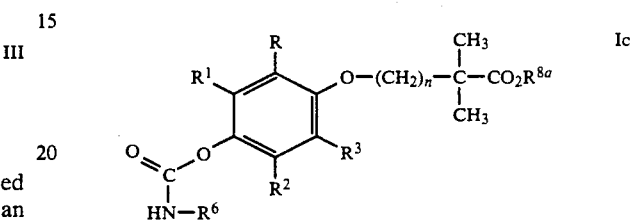   Ic wherein R, $R^1$, $R^2$, $R^3$, $R^6$, $R^{8a}$, and n are as defined above may be prepared by reacting a compound of Formula IV

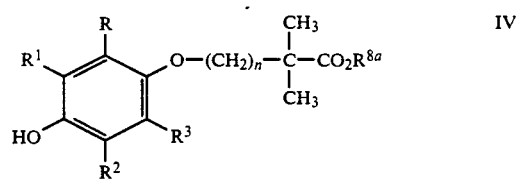   IV wherein R, $R^1$, $R^2$, $R^3$, $R^{8a}$, and n are as defined above with a compound of Formula V

 $R^6NCO$   V wherein $R^6$ is as defined above in a solvent such as, for example, tetrahydrofuran and the like optionally containing a catalytic amount of a base such as, for example, 4-dimethylaminopyridine and the like at about 25° C. to about the reflux temperature of the solvent for about 1 hour to about 24 hours to afford a compound of Formula Ic. Preferably, the reaction is carried out in tetrahydrofuran in the presence of a catalytic amount of 4-dimethylaminopyridine at reflux for about 18 hours.

Preferably, a compound of Formula Id

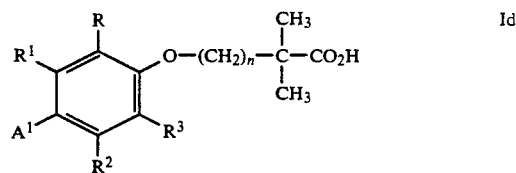   Id wherein $A^1$ is $-OR^5$ wherein $R^5$ is alkyl of from one to four carbon atoms, $-OCH_2R^6$ wherein $R^6$ is aryl,

wherein $R^7$ is alkyl of from one to twenty carbon atoms, or

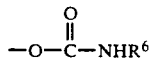

wherein $R^6$ is as defined above, and R, $R^1$, $R^2$, $R^3$, and n are as defined above may be prepared by reacting a compound of Formula Ib or Ic with a base such as, for example, an alkali metal hydroxide, for example, sodium hydroxide, potassium hydroxide, and the like in a solvent such as, for example, an alcohol such as, for example, methanol and the like at about 25° C. to about the reflux temperature of the solvent for about 30 minutes to about 24 hours to afford a compound of Formula Id. Preferably, the reaction is carried out with potassium hydroxide in methanol at about reflux for about 18 hours.

Preferably, a compound of Formula Ie

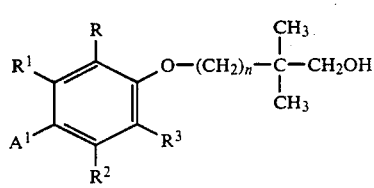

wherein R, $R^1$, $R^2$, $R^3$, $A^1$, and n are as defined above may be prepared by reacting a compound of Formula Ib or Formula Ic with a hydride reagent such as, for example, lithium aluminum hydride and the like in a solvent such as, for example, diethyl ether and the like at about 25° C. to about the reflux temperature of the solvent for about 30 minutes to about 24 hours to afford a compound of Formula Ie. Preferably, the reaction is carried out with lithium aluminum hydride in diethyl ether at reflux for about 4 hours.

A compound of Formula IV is prepared by reacting a compound of Formula If

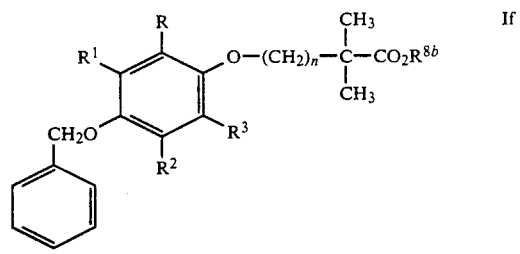

wherein $R^{8b}$ is alkyl of from one to six carbon atoms and R, $R^1$, $R^2 R^3$, and n are as defined above with hydrogen in the present of a catalyst such as, for example, palladium on carbon and the like in a solvent such as, for example, methanol and the like for about 1 to about 24 hours to afford a compound of Formula IV. Preferably, the reaction is carried out in the presence of palladium on carbon in methanol for about 14 hours.

A compound of Formula IIa wherein $R^5$ is alkyl of from one to four carbon atoms, —$CH_2$—$R^6$ wherein $R^6$ is as defined above or

wherein $R^7$ is as defined above, and R, $R^1$, $R^2$, and $R^3$ are as defined above is prepared as outlined in Scheme I.

Thus, a compound of Formula XI wherein R, $R^1$, $R^2$, and $R^3$ are as defined above is reacted with formaldehyde in the presence of a base such as, for example, an alkali metal hydroxide such as sodium hydroxide and the like at about 0° C. to about 50° C. for about 10 minutes to about 8 hours to afford a compound of Formula X wherein R, $R^1$, $R^2$, and $R^3$ are as defined above. Preferably, the reaction is carried out with 35% aqueous formaldehyde solution in the presence of sodium hydroxide at about 0° C. to about 30° C. for about 3 hours.

A compound of Formula X is reacted with oxygen in the presence of a free radical source such as, for example, tetramethyl-1-piperidinyloxy, free radical and the like, and cuprous chloride in a solvent such as, for example, dimethylformamide and the like at about 25° C. for about 1 hour to about 24 hours to afford a compound of Formula IX wherein R, $R^1$, $R^2$, and $R^3$ are as defined above. Preferably, the reaction is carried out in the presence of tetramethyl-1-piperidinyloxy, free radical, and cuprous chloride in dimethylformamide at about 25° C. for about 18 hours.

A compound of Formula IX is reacted with a compound of Formula VIII wherein $R^5$ and Hal are as defined above in the presence of a base such as, for example, an alkali metal carbonate or hydroxide such as potassium carbonate and the like in a solvent such as, for example, acetonitrile and the like at about 25° C. to about the reflux temperature of the solvent for about 1 hour to about 24 hours to afford a compound of Formula VI wherein R, $R^1$, $R^2$, $R^3$, and $R^5$ are as defined above. Preferably, the reaction is carried out in the presence of potassium carbonate in acetonitrile at reflux for about 18 hours.

A compound of Formula VI is reacted with a compound of Formula VII wherein $R^6$ is as defined above in a solvent such as, for example, dichloromethane and the like at about 25° C. to about the reflux temperature of the solvent for about 1 hour to about 24 hours to afford the compound of Formula IIa. Preferably, the reaction is carried out in dichloromethane at reflux for about 16 hours.

A compound of Formula IIb wherein R, $R^1$, $R^2$, $R^3$, and $R^6$ are as defined above is prepared as outlined in Scheme II.

Thus, a compound of Formula XV, wherein R, $R^1$, $R^2$, and $R^3$ are as defined above, is reacted with pivaloyl chloride in the presence of a base such as, for example, pyridine and the like in a solvent such as, for example, dichloromethane and the like at about 0° C. to about 25° C. for about 1 hour to about 48 hours to afford a compound of Formula XIV wherein R, $R^1$, $R^2$, and $R^3$ are as defined above. Preferably, the reaction is carried out in the presence of pyridine in dichloromethane at about 25° C. for about 48 hours.

A compound of Formula XIV is reacted with a compound of Formula XIII wherein $R^6$ and Hal are as defined above using the methodology previously described for converting a compound of Formula XV to a compound of Formula XIV to afford a compound of Formula XII wherein R, $R^1$, $R^2$, $R^3$, and $R^6$ are as defined above.

A compound of Formula XII is reacted with a base such as, for example, an alkali metal hydroxide such as potassium hydroxide and the like in a solvent such as, for example, methanol and the like at about 25° C. to about the reflux temperature of the solvent for about 1 hour to about 24 hours to afford a compound of Formula IIb. Preferably, the reaction is carried out with potassium hydroxide in methanol at reflux for about 8 hours.

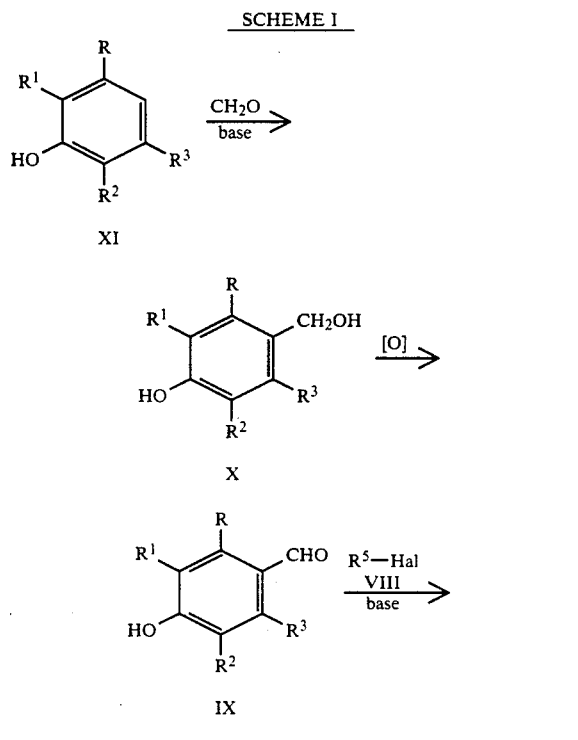

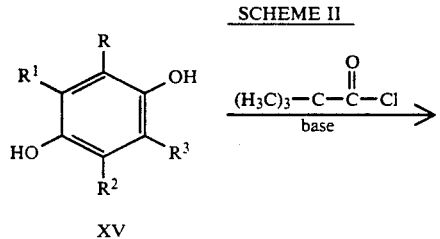

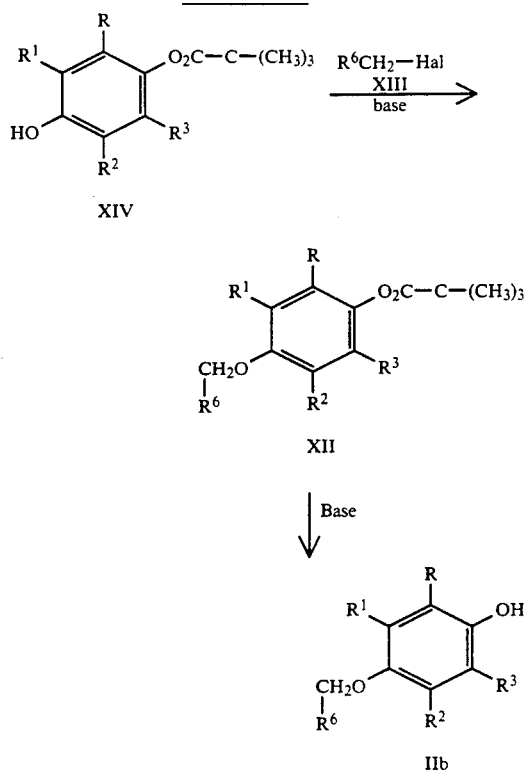

Compounds of Formulas III, IIIa, V, VII, VIII, XI, XIII, and XV are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or Ia or a corresponding pharmaceutically acceptable salt of a compound of Formula I or Ia.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents and the like.

The pharmaceutical preparation is preferably in unit dose form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 50 mg to 1500 mg preferably 200 mg to 500 mg according to the particular application and the potency of the active component. The composition can, if desired, also contain other compatible therapeutic agents.

The dosage range for a 70-kg mammal is from about 1 mg/kg to about 100 mg/kg of body weight per day or preferably about 3 mg/kg to about 15 mg/kg of body weight per day when the compounds of the present invention are used therapeutically as antihypercholesterolemic and antiatherosclerotic agents. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dosage of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

5-(4-Methoxy-2,5-dimethylphenoxy)-2,2-dimethyl-pentanoic acid, methyl ester

A 500 mL, 3 neck round bottom flask is charged with 7.6 g (50 mmol) of 4-methoxy-2,5-xylenol, 8.3 g (60 mmol) of anhydrous potassium carbonate 13.4 g (60 mmol) of 5-bromo-2,2-dimethylvaleric acid, methyl ester (U.S. Pat. No. 4,665,226) and 150 mL of acetonitrile. The mixture is stirred mechanically at reflux for 24 hours. The reaction flask and inorganic solids are washed with fresh acetonitrile and the filtrate evaporated. The residue is taken up in diethyl ether and the solution washed with 50 mL of 2N potassium hydroxide solution, brine, dried (magnesium sulfate) and evaporated. The crude product amounts to 16.6 g. Distillation through a short path apparatus first at aspirator pressure and then at 0.5 mm affords 12.9 g of the title compound; infrared spectrum (IR) (C=0) 1732 cm$^{-1}$.

In a process analogous to Example 1 using appropriate starting materials the corresponding compounds of Formula I (Examples 2 and 3) are prepared as follows:

EXAMPLE 2

5-(4-Butoxy-2,5-dimethylphenoxy)-2,2-dimethylpentanoic acid, methyl ester; bp 164°-166° C./0.5 mm.

EXAMPLE 3

5-(4-Ethoxy-2,5 dimethylphenoxy)-2,2 dimethylpentanoic acid, methyl ester; bp 145°-148° C./0.5 mm.

EXAMPLE 4

5-(4-Methoxy-2,5-dimethylphenoxy)-2,2-dimethylpentanoic acid

A solution containing 11.8 g (40.1 mmol) of 5-(4-methoxy-2,5-dimethylphenoxy)-2,2-dimethylpentanoic acid, methyl ester (Example 1), 40 mL of 2N potassium hydroxide and 150 mL of methanol is stirred at reflux for 18 hours overnight. The methanol is removed on a rotary evaporator and the aqueous solution diluted with water. After the aqueous solution is extracted with diethyl ether it is acidified with excess 6N hydrochloric acid solution and the precipitate is isolated with diethyl ether. The diethyl ether solution is washed with brine, dried (magnesium sulfate) and evaporated leaving a crystalline residue. Recrystallization from 50 mL of acetonitrile in the presence of charcoal affords after refrigeration, 9.7 g of the title compound as colorless crystals; mp 85°-86° C.

In a process analogous to Example 4 using appropriate starting materials the corresponding compounds of Formula I (Examples 5 and 6) are prepared as follows:

EXAMPLE 5

5-(4-Butoxy-2,5-dimethylphenoxy)-2,2-dimethylpentanoic acid; mp 56°-57° C.

EXAMPLE 6

5-(4-Ethoxy-2,5-dimethylphenoxy)-2,2-dimethylpentanoic acid; mp 102°-103° C.

EXAMPLE 7

5-[4-(2,2-Dimethyl-1-oxopropoxy)-2,3,6-trimethylphenoxy]-2,2 dimethylpentanoic acid, methyl ester A mixture of 11.8 g (50 mmol) of 2,2-dimethylpropanoic acid, 4-hydroxy-2,3,6-trimethylphenyl ester (Example A), 13.4 g (60 mmol) of 5-bromo-2,2-dimethylvaleric acid, methyl ester (U.S. Pat. No. 4,665,226) and 8.3 g (60 mmol) of anhydrous potassium carbonate in 150 mL of acetonitrile is stirred at reflux for 18 hours overnight. The solids are removed and the reaction flask and solids are washed with fresh acetonitrile. The solvent is removed on a rotary evaporator and the diethyl ether solution of the residue is washed with 2×50 mL 2N potassium hydroxide solution, brine, then dried and evaporated leaving 21.9 g of a light brown oil. This is treated a second time with 13.4 g (60 mmol) of the bromoester and 8.3 g (60 mmol) of anhydrous potassium carbonate in 150 mL acetonitrile. After stirring at reflux for 72 hours the solids are removed, washed with fresh acetonitrile and the filtrate evaporated. The residue is dissolved in diethyl ether and the solution is washed with water, brine, dried (magnesium sulfate) and evaporated leaving 31.3 g of a pale yellow viscous oil. The crude product is distilled through a short path apparatus. The distillate is chromatographed on a 4.5 cm column containing 225 g of silica gel prepared in 15:1 hexane:tertiary-butyl methyl ether. A series of 200 mL fractions is collected by eluting the column with the same solvent to afford 10.3 g of the title compound; mp 46°-47° C. Thin layer chromatography (TLC) (10:1 hexane:tertiarybutyl methyl ether)

EXAMPLE 8

2,2-Dimethyl-5-[2,3,5-trimethyl-4-(phenylmethoxy)phenoxy]pentanoic acid, methyl ester A 2-1, 3 neck, round bottom flask equipped with an overhead stirrer is charged with 29.4 g (12mmol) of 2,3,5-trimethyl-4-(phenylmethoxy)phenol (Example C), 29.8 g (1.1×12.1 mmol) of 5-bromo-2,2-dimethylvaleric acid, methyl ester (U.S. Pat. No. 4,665,226), 20.1 g (1.2×121 mmol) of anhydrous potassium carbonate and 300 mL of acetonitrile. The heterogeneous mixture is stirred at reflux for 96 hours. The solid is removed and the reaction flask and filtered solids are washed with fresh acetonitrile, the solvent removed and the residue taken up in 500 mL of hexane. On standing the product crystallizes partially and a seed crystal is retained. The solution is diluted to 700 mL with hexane and warmed to dissolve the product. After washing with 2×75 mL of 2N potassium hydroxide solution, and brine the solution is dried and evaporated leaving 46.5 g of a pale yellow solid. This crystallizes from 500 mL of hexane in the presence of charcoal and the solution is cooled to 0° C. and seeded to afford 41.4 g of the title compound as a colorless solid; mp 67°-68° C.

EXAMPLE 9

2,2-Dimethyl-5-[2,3,5-trimethyl-4-(phenylmethoxy)-phenoxy]pentanoic acid

A solution of 9.6 g (25 mmol) of 2,2-dimethyl-5-[2,3,5-trimethyl-4-(phenylmethoxy)phenoxy]pentanoic acid, methyl ester (Example 8) and 2.8 g (2×25 mmol) of potassium hydroxide in 150 mL of methanol is stirred at reflux for 18 hours overnight. The methanol is removed on a rotary evaporator and the residue diluted with 200 mL of water. The aqueous solution is stirred with 100 mL, then 50 mL of diethyl ether. The diethyl ether layers are combined, washed with brine, dried (magnesium sulfate) and evaporated leaving 3.4 g of recovered methyl ester. The aqueous layer is acidified with 15 mL of 6N hydrochloric acid solution and the product acid is isolated with diethyl ether. The diethyl ether solution is washed with brine, dried (magnesium sulfate) and evaporated leaving 5.9 g of crystalline product. Recrystallization from 50 mL of acetonitrile, concentration to 35 mL and refrigeration affords 8.6 g of the title compound as colorless crystals; mp 105°-107° C.

EXAMPLE 10

2,2-Dimethyl-5-2,3,5-trimethyl 4-(phenylmethoxy)-phenoxy-]pentanol

A solution of 7.7 g (20 mmol) of 2,2 dimethyl-5-[2,3,5-trimethyl-4-(phenylmethoxy)phenoxy]pentanoic acid, methyl ester (Example 8) in 100 mL diethyl ether is added to a mixture of 0.8 g (20 mmol) of lithium aluminum hydride in 100 mL of diethyl ether. When the addition is complete (5 min) the mixture is stirred at reflux for 4 hours then the mixture is worked up (addition of n mL of water, n mL of 15% sodium hydroxide solution, 2n mL of water for n g of lithium aluminum hydride). The reaction flask and collected solid are washed with fresh diethyl ether and the filtrate is evaporated leaving 7.4 g of a colorless oil which crystallizes on standing, mp 67°-69° C. Recrystallization from 75 mL of hexane affords 6.8 g of the title compound as a colorless solid; mp 81°-83° C.

EXAMPLE 11

5-[3,5-Dimethyl-4-(phenylmethoxy)phenoxy]-2,2-dimethylpentanoic acid, methyl ester A mixture of 11.3 g (49.6 mmol) of 3,5-dimethyl-4-(phenylmethoxy)phenol (Example G), 13.3 g (1.2×49.6 mmol) of 5-bromo-2,2-dimethylvaleric acid, methyl ester (U.S. Pat. No. 4,665,226) and 8.2 g (1.2×49.6 mmol) of anhydrous potassium carbonate in 300 mL of acetonitrile is stirred at reflux for 18 hours. The reaction flask and inorganic residue are washed with fresh acetonitrile and the solvent is removed. A diethyl ether solution of the residual product is washed with 50 mL of 2N potassium hydroxide solution, brine, dried and evaporated leaving 20.6 g of the product as a pale yellow oil. Distillation through a short path apparatus affords 15.4 g of the title compound; bp 190°-194° C./0.1 mm (230°-240° C).

EXAMPLE 12

5-[3,5-Dimethyl-4-phenylmethoxy)phenoxy]-2,2-dimethylpentanoic acid

A solution of 8.7 g (23.5 mmol) of 5-[3,5-dimethyl-4-(phenylmethoxy)phenoxy]-2,2-dimethylpentanoic acid, methyl ester (Example 11) in 150 mL of methanol and 4.0 g (3×24 mmol) of potassium hydroxide in 25 mL water is stirred at reflux for 18 hours overnight. The methanol is removed on a rotary evaporator, the residual aqueous solution is diluted with 100 mL of water, back extracted with diethyl ether and the aqueous layer is acidified with 25 mL of 6N hydrochloric acid solution. The precipitate is isolated with diethyl ether, the solution is washed with brine, dried (magnesium sulfate) and evaporated yielding 7.6 g of a brown oil which crystallizes on standing. Recrystallization from 35 mL of acetonitrile affords 4.9 g of the title compound as tan crystals; mp 96°–97° C.

EXAMPLE 13

5-[2,5-Dimethyl-4-(phenylmethoxy)phenoxy]-2,2-dimethylpentanoic acid, methyl ester A 1 liter, 3 neck round bottom flask fitted with an overhead stirrer is charged with 100 mL of dimethylsulfoxide and 6.0 g of 60% sodium hydride, washed free of mineral oil with toluene (3.6 g contained; 150 mmol), then a solution of 34.2 g 150 mmol) of 2,5-dimethyl-4-(phenylmethoxy)-phenol (Example K) in 200 mL of toluene is added at 20°–25° C. When hydrogen evolution is complete, 40.1 g (1.2×150 mmol) of 5 bromo-2,2 dimethylvaleric acid, methyl ester (U.S. Pat. No. 4,665,226) is added and the temperature is raised to 75° C. When the temperature reaches 55° C., a solid separates (sodium phenolate). After 18 hours overnight the mixture is heated to reflux for 4 hours; then the mixture is cooled and 200 mL of water is added. The aqueous layer is extracted with diethyl ether and the organic layers are combined and the solution is washed with water, dried (magnesium sulfate) and evaporated leaving 65.7 g of a dark brown oil which crystallizes on standing. Recrystallization from hexane in the presence of charcoal affords 39.5 g of the title compound; mp 75.5°–76.5° C.

EXAMPLE 14

5-[2,5-Dimethyl-4-(phenylmethoxy)phenoxy]-2,2-dimethylpentanoic acid

A solution of 7.8 g (2.1 mmol) of 5-[2,5-dimethyl-4-(phenylmethoxy)phenoxy]-2,2-dimethylpentanoic acid, methyl ester (Example 13), 3.5 g (3×21 mmol) of potassium hydroxide, 10 mL of water and 100 mL of methanol is stirred at reflux for 12 hours. The methanol is removed and the residual aqueous solution is diluted with 150 mL of water then back-extracted with diethyl ether. The aqueous layer is acidified with 15 mL of 6N hydrochloric acid solution and the product is isolated with diethyl ether. The diethyl ether solution is washed with brine, dried (magnesium sulfate) and evaporated leaving 6.9 g of a dark brown crystalline residue. Recrystallization from 30 mL of acetonitrile in the presence of charcoal affords 4.0 g of the title compound as tan, dense crystals; mp 104°–106° C.

EXAMPLE 15

5-[4-[[[[2,6-Bis(1-methylethyl)phenyl]amino]carbonyl]oxy]-2,5-dimethylphenoxy]-2,2-dimethylpentanoic acid, methyl ester Step A: Preparation of 5-(4-Hydroxy-2,5-dimethylphenoxy)-2,2-dimethylpentanoic acid, methyl ester A solution of 1.85 g (5 mmol) of 5-[2,5-dimethyl-4-(phenylmethoxy)phenoxy]-2,2-dimethylpentanoic acid, methyl ester (Example 13) in 100 mL of methanol and 0.2 g of 20% palladium on carbon is shaken under a hydrogen atmosphere of 50 pounds per square inch (psi) for 14 hours. The catalyst is removed and the solvent is evaporated to afford the title compound as a colorless oil (1.5 g).

Step B: Preparation of 5-[4-[[[[2,6-Bis(1-methylethyl)phenyl]amino]carbonyl]oxy]-2,5-dimethylphenoxy]-2,2-dimethylpentanoic acid, methyl ester A mixture of 5-(4-hydroxy-2,5-dimethylphenoxy)-2,2-dimethylpentanoic acid, methyl ester, 1.5 g and 1.0 g (5 mmol) of 2,6-diisopropylphenylisocyanate in 75 mL of tetrahydrofuran containing 0.1 g of 4-dimethylaminopyridine is stirred at reflux for 18 hours overnight. The solvent is removed leaving 3.1 g of the title carbamate which crystallizes on standing. The crude precipitate is chromatographed on a 4.5 cm column containing 125 g of silica gel prepared in 1:1 hexane:dichloromethane. Elution with dichloromethane affords 1.8 g of the title compound. Recrystallization from 75 mL of hexane affords the title compound as a colorless solid; mp 111°–112° C.

PREPARATION OF STARTING MATERIALS

EXAMPLE A 2,2-Dimethylpropanoic acid, 4-hydroxy-2,3,6-trimethylphenyl ester

A 500 mL round bottom flask is equipped with a stirring bar and charged with 15.2 g (100 mmol) of trimethylhydroquinone and 23.7 g (3×100 mmol) of pyridine in 100 mL dichloromethane. The solution is stirred at ambient temperature and a solution of 20.8 g (100 mmol) of pivaloyl chloride in 100 mL of dichloromethane is added over 15 minutes. The final solution is stirred at ambient temperature for 48 hours, then washed with 1×100 mL of 3N hydrochloric acid solution, 1×50 mL of 3N hydrochloric acid solution, water, dried (magnesium sulfate) and evaporated leaving 26.6 g (>100%) of a pale yellow solid, mp 88°–112° C. (after drying 24.1 g). Recrystallization from hexane in the presence of charcoal affords the title compound as colorless cubes; mp 119°–121° C.

EXAMPLE B 2,2-Dimethylpropanoic acid, 2,3,5-trimethyl-4-(phenylmethoxy)phenyl ester A mixture of 43.5 g (184 mmol) of 2,2-dimethylpropanoic acid, 4-hydroxy-2,3,6-trimethylphenyl ester (Example A), 23.4 g (184 mmol) of benzyl chloride and 30.5 g (1.2×184 mmol) of anhydrous potassium carbonate in 500 mL of acetonitrile is stirred at reflux for 70 hours. The solid is removed and the reaction flask and solid are washed with fresh acetonitrile and the solvent removed on a rotary evaporator. The crude product amounts to 60.5 g which crystallizes on standing, mp 50°–53° C. Recrystallization from methanol in the presence of charcoal affords the title compound; mp 58°–59° C.

EXAMPLE C 2,3,5-Trimethyl-4-(phenylmethoxy)phenol

A solution of 20.8 g (2.1×177 mmol) of potassium hydroxide in 100 mL of water is added to a solution of 57.8 g (177 mmol) of 2,2-dimethylpropanoic acid, 2,3,5- trimethyl-4-(phenylmethoxy)phenyl ester (Example B) in 300 mL of methanol. The solution is stirred at reflux for 6 hours, then permitted to stir at ambient temperature for another 8 hours. The solvent is removed on a rotary evaporator and the residual aqueous solution (dark brown) is diluted with 100 mL of water and acidified with excess 6N hydrochloric acid solution (40 mL). The product is isolated with diethyl ether and the diethyl ether solution is washed with 2×100 mL saturated (10%) sodium bicarbonate solution, brine, dried (magnesium sulfate) and evaporated leaving 48.4 g of crude product as a light brown solid. Chromatography on a 6.5 cm column containing 350 g of silica gel prepared in toluene and elution with 95% toluene:5% ethyl acetate affords 30.6 g of the title compound; mp 101°–103° C.

EXAMPLE D

4-Hydroxy-3,5-dimethyl-benzenemethanol

A 1-L, 3 neck, round bottom flask is charged with 24.2 g (200 mmol) of 2,6-dimethylphenol, 12.0 g (200 mmol) of sodium hydroxide and 150 mL of water. The solution is cooled to 0° C. and 85 mL of a 35% aqueous formaldehyde solution (30 g contained; 5×200 mmol) is added over 10 minutes. The temperature is maintained for 30 minutes, then the ice bath is removed for 30 minutes, and finally the mixture is warmed to 30° for 3 hours. Near the conclusion of the reaction period some crystalline solid separates. The solid is collected, washed thoroughly with water and dried in vacuo at 40° C. The orange solution is acidified with 18 g (300 mmol) of acetic acid and the product isolated with diethyl ether. The diethyl ether solution is washed with brine, dried (magnesium sulfate) and evaporated leaving 23.8 g of a yellow oil which crystallizes when seeded with the solid isolated above. The nuclear magnetic resonance spectrum (NMR) is consistent with the title compound. Recrystallization from toluene affords the title compound as white needles; mp 102°–104° C.

In a process analogous to Example D using appropriate starting materials a corresponding compound (Example $D_a$) is prepared as follows:

EXAMPLE Da

4-Hydroxy-2,5-dimethylbenzenemethanol; mp 164°–165° C. (d).

EXAMPLE E

4-Hydroxy-3,5-dimethyl-benzaldehyde

A mixture of 23.8 g (153 mmol) of 4 hydroxy-3,5-dimethyl-benzenemethanol (Example D), 1.2 g (0.05×153 mmol) of TEMPO (tetramethyl-1-piperidinyloxy, free radical) (Aldrich) and 0.76 g (0.05×153 mmol) of cuprous chloride in 300 mL of dimethylformamide is stirred vigorously under an atmosphere of oxygen (maintained by a balloon) at ambient temperature for 18 hours overnight. A homogeneous solution is obtained (all cuprous chloride dissolved-)—dark green in dimethylformamide. The dimethylformamide is removed on a rotary evaporator and the solid residue taken up in diethyl ether. The diethyl ether solution is washed with 2×50 mL of 2N hydrochloric acid solution, brine, dried (magnesium sulfate) leaving 20.8 g of crude precipitate as a tan solid. Recrystallization from 350 mL of cyclohexane containing 20% dichloromethane in the presence of charcoal affords 11.2 g of the title compound as yellow leaflets; mp 114°–116° C.

In a process analogous to Example E using appropriate starting materials, a corresponding compound (Example $E_a$) is prepared as follows:

EXAMPLE Ea

4-Hydroxy-2,5-dimethylbenzaldehyde; mp 133°–134.5° C.

EXAMPLE F 3,5-Dimethyl-4-(phenylmethoxy)benzaldehyde

A mixture of 4.6 g (30.6 mmol) of 4-hydroxy 3,5-dimethyl benzaldehyde (Example E), 4.4 g (35 mmol) of benzyl chloride and 4.8 g (35 mmol) of anhydrous potassium carbonate in 100 mL of acetonitrile, is stirred at reflux for 18 hours overnight. The reaction flask and the inorganic salts are washed with fresh acetonitrile and the solvent is removed on a rotary evaporator. A diethyl ether solution of the residue is washed with 2×25 mL of 1N potassium hydroxide solution, brine, dried (magnesium sulfate) and evaporated. Distillation through a short path apparatus affords 6.5 g of the title compound; bp 149°–152° C./0.50 mm (190°–195° C).

In a process analogous to Example F using appropriate starting materials, a corresponding compound (Example Fa) is prepared as follows:

EXAMPLE Fa

4-Ethoxy-2,5-dimethylbenzaldehyde; bp 90°–93° C./0.50 mm.

EXAMPLE G 3,5-Dimethyl-4-(phenylmethoxy)phenol

A solution of 18.0 g (75 mmol) of 3,5-dimethyl-4-(phenylmethoxy)benzaldehyde (Example F) and 17.1 g of 85% meta-chloroperbenzoic acid (14.5 g contained; 1.2×75 mmol) in 600 mL of dichloromethane is stirred at reflux for 16 hours. The cooled solution is stirred with 2×150 mL saturated sodium bicarbonate solution, 150 mL of 10% sodium bisulfite solution, then dried (magnesium sulfate) and evaporated leaving 15.2 g of a turbid oil. A solution of the latter in 225 mL of methanol is stirred at ambient temperature with a solution of 12.6 g (3×75 mmol) of potassium hydroxide in 75 mL of water. After 18 hours the methanol is removed on a rotary evaporator and the residual aqueous solution is diluted with 200 mL of water, and back-extracted with 150 mL of diethyl ether. The aqueous solution is acidified with 50 mL of 6N hydrochloric acid solution and the product is isolated with diethyl ether. The diethyl ether solution is washed with brine, dried (magnesium sulfate) and evaporated leaving 8.1 g of a brown solid. The original diethyl ether extract is dried (magnesium sulfate) and evaporated leaving 10.7 g of a light yellow viscous oil. The two fractions are combined and the crude precipitate is chromatographed on a 4.5 cm column containing 250 g of silica gel prepared in toluene. Elution with 98% toluene:2% ethyl acetate affords 16.6 g of the product. Recrystallization from cyclohexane affords the title compound as off-white leaflets; mp 89°–91° C.

In a process analogous to Example G using appropriate starting materials, a corresponding compound (Example Ga) is prepared as follows:

EXAMPLE Ga

4-Ethoxy-2,5-dimethylphenol;

EXAMPLE H

4-Hydroxy-2,5-dimethyl-benzenemethanol

A 1-L, 3 neck, round bottom flask is charged with 24.4 g (200 mmol) of 2,5 dimethylphenol, 8.0 g (200 mmol) of sodium hydroxide and 150 mL water. The mixture is warmed to 50° C. until the phenol dissolves, then cooled to 10° C. and 34 mL of 36% aqueous formaldehyde is added over 10 minutes. The ice bath is removed and the solution is permitted to stir at ambient temperature for 2 hours, then warmed to 30° C. for 2 hours. The reaction solution is cooled to 10° C., 18 g (300 mmol) of acetic acid is added and the product is isolated with diethyl ether and ethyl acetate. The organic layers are combined and the solution is washed with brine, dried (magnesium sulfate) and evaporated leaving 29.8 g of a tan solid consisting of two products. The crude precipitate is chromatographed on a 6.0 cm column containing 350 g of silica gel prepared in toluene. The crude product is placed on the column as a solution in 500 mL of toluene + 15% of tetrahydrofuran. A series of 500 mL fractions is collected by eluting the column with toluene + 15% tetrahydrofuran to afford 18.3 g of a colorless solid. Recrystallization from acetonitrile in the presence of charcoal affords the title compound; mp 164°–165° C.

EXAMPLE I 2,5-Dimethyl-4-(phenylmethoxy)benzenemethanol

A mixture of 18.0 g (118 mmol) of 4-hydroxy-2,5-dimethyl-benzenemethanol (Example H), 14.9 g (118 mmol) of benzyl chloride and 18.0 g (1.1 × 118 mmol) of anhydrous potassium carbonate in 300 mL of acetonitrile is stirred at reflux for 18 hours overnight. The reaction flask and inorganic residue are washed with fresh acetonitrile and the solvent is removed on a rotary evaporator. A diethyl ether solution of the residue is washed with 2 × 50 mL of 2N potassium hydroxide solution, brine, dried (magnesium sulfate) and evaporated leaving 28.3 g of a pale yellow viscous residue. Distillation through a short path apparatus affords the title compound; mp 58°–59° C.

EXAMPLE J 2,5-Dimethyl-4-(phenylmethoxy)benzaldehyde

A mixture of 11.0 g (46 mmol) of 2,5-dimethyl-4-(phenylmethoxy)benzenemethanol (Example I), 0.4 g (0.05 × 46 = 2.3 mmol) of TEMPO (tetramethyl-1-piperidinyloxy, free radical) (Aldrich) and 0.2 g (2.3 mmol) of cuprous chloride in 150 mL of dimethylformamide is stirred vigorously under an atmosphere of oxygen (maintained by a balloon) at ambient temperature for 18 hours overnight. The heterogeneous mixture is (dark green) filtered through a pad of celite, washed with diethyl ether and the solvents are removed on a rotary evaporator. The residue is dissolved in diethyl ether and the solution is washed with 2 × 50 mL of 2N hydrochloric acid solution, brine, dried (magnesium sulfate) and evaporated leaving 10.7 g of a yellow viscous residue. Distillation of the product through a short path apparatus affords 10.3 g of a pale yellow distillate, bp 156°–8° C./0.50 (175°–180° C.) on standing the product crystallizes; mp 48°–49° C.

EXAMPLE K 2,5-Dimethyl-4-(phenylmethoxy)phenol

A solution of 6.7 g (28 mmol) of 2,5-dimethyl-4-(phenylmethoxy)benzaldehyde (Example J), and 6.8 g of 85% meta-chloroperbenzoic acid (5.8 g contained; 1.2 × 28 mmol) in 250 mL of methylene chloride is stirred at reflux for 12 hours. The cooled solution is stirred with 2 × 75 mL of saturated sodium bicarbonate solution, 50 mL of 10% sodium bisulfite solution, 100 mL of water, then dried (magnesium sulfate) and evaporated leaving 7.7 g of a yellow oil. A solution of the latter oil in 75 mL of methanol is stirred at ambient temperature with a solution of 4.7 g (3 × 28 mmol) of potassium hydroxide in 25 mL water. A brown solution is produced immediately. After 18 hours the methanol is removed on a rotary evaporator and the residual material is diluted with 200 mL water then stirred with 2 × 150 mL diethyl ether. The aqueous layer is acidified with 20 mL of 6N hydrochloric acid solution and the product is isolated with diethyl ether. The diethyl ether solution is washed with brine, dried (magnesium sulfate) and evaporated leaving 1.1 g of a dark brown semi-solid residue. The original diethyl ether extracts are washed with brine, dried (magnesium sulfate) and evaporated leaving 5.6 g of a light yellow solid. Recrystallization from 50 mL of cyclohexane in the presence of charcoal affords 4.7 g of the title compound as a colorless solid; mp 92°–93° C.

EXAMPLE L

1-Butoxy-2,5-dimethyl-4-(phenylmethoxy)benzene

A mixture of 13.4 g (59 mmol) of 2,5-dimethyl-4-(phenylmethoxy)phenol (Example K), 9.7 g (1.2 × 59 mmol) of butyl bromide and 12.2 g (1.5 × 59 mmol) of anhydrous potassium carbonate in 150 mL of acetonitrile is stirred at reflux for 40 hours. The reaction flask and inorganic residue are washed with acetonitrile and the filtrate is evaporated. Chromatography on a 3.5 cm column containing 175 g of basic alumina (activity grade I) prepared in 2:1 hexane-toluene and elution with the same solvent affords 13.1 g of the title compound; bp 153°–155° C./0.50 mm (mp 185°–195° C).

EXAMPLE M

4-Butoxy-2,5-dimethylphenol

A solution of 11.2 g (39.5 mmol) of 1 butoxy-2,5-dimethyl-4-(phenylmethoxy)benzene (Example L) in 100 mL of methanol containing 1 g of 20% palladium on carbon is shaken under three atmospheres of hydrogen for 1 hour. The catalyst is removed and the solvent evaporated in vacuo to afford 7.6 g of the title compound; mp 43°–45° C.

I claim:

1. A compound of Formula I

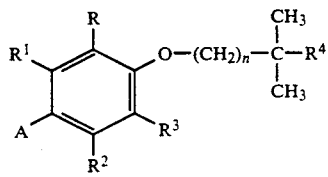

wherein A is

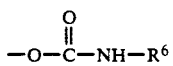

wherein $R^6$ is aryl;

R, $R^1$, $R^2$, and $R^3$ are each independently hydrogen or alkyl of from one to six carbon atoms provided at least two of R, $R^1$, $R^2$, or $R^3$ are alkyl of from one to six carbon atoms;

n is an integer of 3, 4, 5, or 6;

$R^4$ is $-CO_2R^8$ wherein $R^8$ is hydrogen, alkyl of from one to six carbon atoms, or benzyl, or $-CH_2OH$; or a pharmaceutically acceptable base salt thereof.

2. A compound according to claim 1, in which R, $R^1$, $R^2$, and $R^3$ are each independently hydrogen or methyl provided at least two of R, $R^1$, $R^2$, or $R^3$ are methyl.

3. A compound according to claim 2, in which R, $R^1$, $R^2$, and $R^3$ are each independently hydrogen or methyl provided at least two of R, $R^1$, $R^2$, or $R^3$ are methyl and n is an integer of 3.

4. A compound according to claim 3 which is 5-[4-[[[[2,6-Bis (1-methylethyl)phenyl[-amino]carbonyl]oxy]-2,5-dimethylphenoxy]-2,2-dimethylpentanoic acid, methyl ester.

5. A method of treating hypercholesterolemia or atherosclerosis comprising administering to a mammal in need of such treatment an acyl-coenzyme A:cholesterol acyltransferase-inhibitory effective amount of a compound of Formula Ia

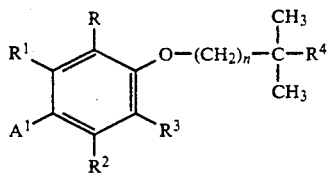

wherein $A^1$ is $-OR^5$ wherein $R^5$ is alkyl of from one to four carbon atoms, $-O-CH_2R^6$ wherein $R^6$ is aryl,

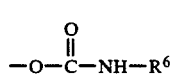

wherein $R^7$ is lower alkyl of from one to twenty carbon atoms, or $$-O-\overset{O}{\underset{\|}{C}}-NH-R^6$$

wherein $R^6$ is as defined above; R, $R^1$, $R^2$, and $R^3$ are each independently hydrogen or alkyl of from one to six carbon atoms provided at least two of R, $R^1$, $R^2$, or $R^3$ are alkyl of from one to six carbon atoms;

n is an integer of 3, 4, 5, or 6;

$R^4$ is $CO_2R^8$ wherein $R^8$ is hydrogen, alkyl of from one to six carbon atoms, or benzyl, or $-CH_2OH$; or a pharmaceutically acceptable base addition salt thereof in unit dosage form.

6. A pharmaceutical composition for treating hypercholesterolemia or atherosclerosis comprising an acyl-coenzyme A:cholesterol acyltransferase-inhibitor effective amount of a compound as defined in claim 1 in combination with a pharmaceutically acceptable carrier.

* * * * *